United States Patent [19]

Kimmel et al.

[11] Patent Number: 4,863,694
[45] Date of Patent: * Sep. 5, 1989

[54] CHEMICALLY SENSITIVE COMPONENT

[75] Inventors: Heinrich Kimmel, Buckenhof; Bernhard Montag, Forchheim; Walter Gumbrecht, Erlangen, all of Fed. Rep. of Germany

[73] Assignee: Siemens Aktiengesellschaft, Munich, Fed. Rep. of Germany

[*] Notice: The portion of the term of this patent subsequent to Jun. 21, 2005 has been disclaimed.

[21] Appl. No.: 833,727

[22] Filed: Feb. 26, 1986

[30] Foreign Application Priority Data

Feb. 26, 1985 [DE] Fed. Rep. of Germany ....... 3506676
Feb. 26, 1985 [DE] Fed. Rep. of Germany ....... 3506686
Feb. 26, 1985 [DE] Fed. Rep. of Germany ....... 3506684

[51] Int. Cl.$^4$ .............................. G01N 21/77
[52] U.S. Cl. ...................... 422/86; 422/91; 422/52; 422/56; 422/57; 436/169; 436/172
[58] Field of Search ............... 422/86, 87, 91, 52, 422/55, 56, 57; 436/164, 169, 172

[56] References Cited

U.S. PATENT DOCUMENTS

| | | |
|---|---|---|
| 3,114,610 | 12/1963 | Gafford et al. ............... 422/86 |
| 3,397,966 | 8/1968 | Plantz . |
| 3,455,656 | 7/1969 | Roberts et al. ............... 422/86 |
| 3,754,867 | 8/1973 | Guenther . |
| 3,873,269 | 3/1975 | Kraffczyk et al. . |
| 3,920,402 | 11/1975 | Afanasiev et al. . |
| 4,115,067 | 9/1978 | Lyshkow ..................... 422/86 X |
| 4,248,597 | 2/1981 | McNeely . |
| 4,251,223 | 2/1981 | White . |
| 4,258,000 | 3/1981 | Obermayer . |
| 4,362,645 | 12/1982 | Hoff et al. . |
| 4,398,183 | 8/1983 | Ando . |
| 4,407,960 | 10/1983 | Tratnyek . |
| 4,436,819 | 3/1984 | Manning . |
| 4,447,542 | 5/1984 | Gantzer . |
| 4,478,792 | 10/1984 | McConnaughey et al. . |
| 4,485,665 | 12/1984 | Norman . |
| 4,567,019 | 1/1986 | Lawton . |
| 4,587,100 | 5/1986 | Amano et al. . |

Primary Examiner—Barry S. Richman
Assistant Examiner—Lynn M. Kummert
Attorney, Agent, or Firm—Kenyon & Kenyon

[57] ABSTRACT

The present invention is directed to a chemically sensitive component including an optical filter that reversibly changes color or transparency in response to a gas or vapor to be determined or detected. The optical filter comprises a mixture of a basic or acid color former or dye of the triphenyl methane system and a complementary acid or basic compound which may be embedded in a matrix and/or applied as a coating to a carrier. The optical filter's change in color or transparency can be measured photoelectronically, e.g., with a luminescent diode as a light source and a photodiode or a phototransistor as a light detector.

19 Claims, 1 Drawing Sheet

CHEMICALLY SENSITIVE COMPONENT

FIELD OF THE INVENTION

The present invention relates to a chemically sensitive component for the determination and detection of various gases and vapors.

BACKGROUND OF THE INVENTION

Various methods for the detection and determination of gases and vapors are known, such as, test tube methods which require a separate test tube for each test and mass spectral analysis which requires expensive equipment. Although mass spectral analysis is a very accurate and precise method such high precision and accuracy is often not necessary for such measurements.

Less expensive and hitherto known methods employ chemically sensitive sensors such as metal spirals or metal oxide semiconductors which can only be used at high temperatures and are only useful for measuring a few gases or vapors, e.g., oxygen in automobile exhaust, relative humidity, flue gas, or the determination of hydrogen or oxygen.

OBJECTS AND SUMMARY OF THE INVENTION

It is an object of the present invention to provide relatively inexpensive chemically sensitive components for the qualitative and/or quantitative determination and/or detection of various gases and vapors and that are of suitable size and cost for use in integrated circuits (IC).

The present invention provides a chemically sensitive component for the determination and detection of gases and vapors which comprises a light source, a detector means, and an optical filter that reversibly changes color and/or transparency in response to the vapor pressure of a gas or vapor to be measured and said optical filter being disposed with respect to the detector means and light source so that the detector means can measure the changes in said optical filter. The optical filter comprises a mixture of at least one compound selected and from the group consisting of basic and acid color formers and at least one compound selected from the group consisting of complementary acids and bases. Said mixture may be applied to a carrier or embedded in a matrix.

DETAILED DESCRIPTION OF THE INVENTION

The optical filter that reversibly changes color and/or transparency when exposed to a gas or vapor constituent to be detected or measured comprises a mixture of at least one basic or acid color former, e.g., dyes from the triphenyl methane system or sulfone phthalein, and at least one complementary basic compound, e.g., p-toluidine or p-chloraniline or complementary acid compound, e.g. bisphenol A or salicylic acid. The mixture may be applied to a surface or embedded in a matrix.

Optical filters useful in the practice of this invention are described in U.S. Patent No. 4,752,447 the text of which is incorporated herein by reference.

A preferred optical filter is a mixture of a triphenyl methane color former and bisphenol A or salicylic acid. Another, preferred optical filter for the determination of ammonia and solvent vapors includes at least one dye such as crystal violet or bromothymol blue and at least one complementary acid or basic compound. The chemically sensitive components of the invention may be constructed by arranging a radiation, e.g., light, source such as a luminescent diode, incandescent lamp, discharge lamp, chemiluminescent device, photoluminescent device, or the like so that radiation emitted therefrom follows a path to a detector means such as a photodiode, phototransistor, photoresistor, photocell, or the like; with respect to an optical filter prepared as described above and disposed in the path of the emitted radiation so that when the optical filter's color or transparency changes in response to vapors or gases to be detected or measured it causes a measurable change in the radiation reaching the detector means, e.g., intensity. Changes in the radiation reaching the detector means are converted to a measurable electrical signal which may be correlated to the partial pressure of the gas or vapor detected.

The optical filters employed in this invention are sensitive to or reversibly react with, i.e., change color or transparency, in response to numerous gases, e.g., ammonia, and vapors, particularly solvent vapors, e.g., acetone, alcohol, chloroform, or ethylacetate vapors; and provide detection limits as low as about 10 ppm.

The carriers and matrices used in making the optical filters may be selected to influence the sensitivity of the optical filter to different gases or vapors.

Figure 1:
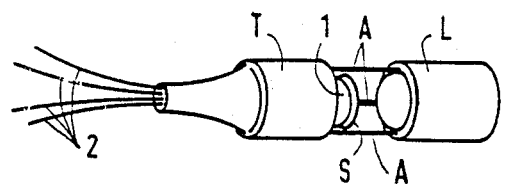
FIG. 1 is a perspective view of a chemically sensitive component constructed in accordance with the present invention.

Referring now to FIG. 1 which depicts a chemically sensitive component comprising two cylindrical body parts in which luminescent diode L and phototransistor T are mounted. The cylinders are held in position with respect to each other by spacers A so that light emitted from luminescent diode L follows a path to phototransistor T. Two of the spacers A provide an electric current supply from leads 2 to luminescent diode L. A coating S of a mixture including the above described color former or dye and complementary acid or basic compound is applied directly to front lens 1 of phototransistor T. When the coating S is exposed to a gas or vapor that changes the color or transparency of the mixture the intensity of the light reaching the phototransistor T is altered causing a measurable change in the electrical output of phototransistor T.

Figure 2:
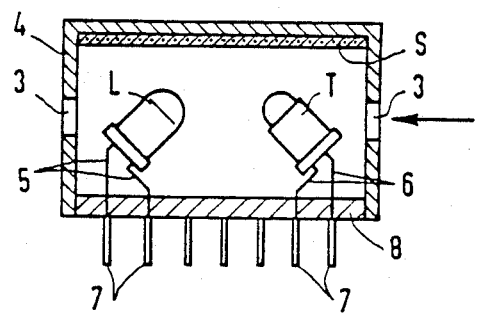
FIG. 2 is a cross-sectional side view of a dual-in-line (DIL) housing incorporating the present invention.

FIG. 2 shows a chemically sensitive component comprising a dual-in-line housing 4 having a plurality of gas or vapor entry holes 3 therein and a coating S of the mixture described above on an interior surface thereof. A phototransistor T and luminescent diode L are disposed within the housing and positioned so that light emitting from the luminescent diode L is reflected and/or scattered from coating S to phototransistor T. Leads 5 and 6 are connected to terminals 7 in base plate 8. When the coating S is exposed to a gas or vapor which causes its color or transparency to change the intensity of the light from luminescent diode L reaching phototransistor T is measurably altered.

Figure 3:
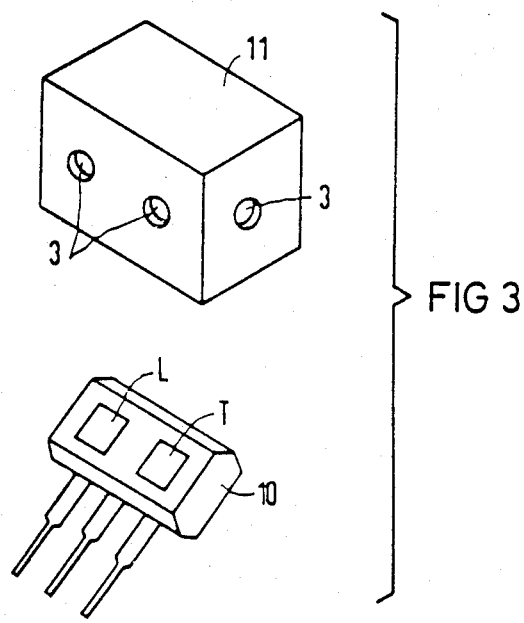
FIG. 3 is a perspective view of a miniature reflex light barrier incorporating the present invention.

FIG. 3 shows a chemically sensitive component comprising a miniature reflex light barrier 10 on which luminescent diode L and phototransistor T are integrated. A coating S of the mixture described above is applied to an upper inside surface of plastic cap 11 which is provided with gas or vapor entry holes 3. Cap 11 fits over light barrier 10 so that coating S is positioned with respect to phototransistor T and luminescent diode L so that when it changes color or transparency in response to a gas or vapor the intensity of light reaching the phototransistor T is measurably altered.

What is claimed is:

1. A chemically sensitive component for measuring gases and vapors comprising a radiation emitting source, a detector means and an optical filter that reversibly changes color or transparency in response to a gas or vapor to be measured; said optical filter comprising a mixture of at least one compound selected from the group consisting of a basic color former or dye and an acid color former or dye and at least one compound selected from the group consisting of a complementary acid and complementary base; said optical filter being disposed so that radiation emitted from said source reaching said detector means is measurably altered by changes in the color or transparency of said optical filter.

2. The chemically sensitive component according to claim 1, wherein the optical filter is a mixture of at least one basic color former from the triphenyl methane system and a complementary acid.

3. The chemically sensitive component according to claim 2 wherein the mixture is applied to a carrier in the form of a coating.

4. The chemically sensitive component according to claim 2 wherein the mixture is embedded in a matrix.

5. The chemically sensitive component according to claim 2 wherein the change in color or transparency of the optical filter is measured photoelectronically.

6. The chemically sensitive component according to claim 1, wherein the acidic or basic color former is a triphenyl methane dye or sulfone phthalein.

7. The chemically sensitive component according to claim 6 wherein the mixture is applied to a carrier in the form of a coating.

8. The chemically sensitive component according to claim 6 wherein the mixture is embedded in a matrix.

9. The chemically sensitive component according to claim 6 wherein the change in color or transparency of the optical filter is measured photoelectronically.

10. The chemically sensitive component according to claim 1, wherein the mixture is applied to a carrier in the form of a coating.

11. The chemically sensitive component according to claim 10, wherein the change in color or transparency of the optical filter is measured photoelectronically.

12. The chemically sensitive component according to claim 11, wherein the radiation source is a luminescent diode and the detector means is a photodiode or phototransistor.

13. The chemically sensitive component according to claim 1 wherein the mixture is embedded in a matrix.

14. The chemically sensitive component according to claim 13, wherein the change in color or transparency of the optical filter is measured photoelectronically.

15. The chemically sensitive component according to claim 14, wherein the radiation source is a luminescent diode and the detector means is a photodiode or phototransistor.

16. The chemically sensitive component according to claim 1, wherein the change in color or transparency of the optical filter is measured photoelectronically.

17. The chemically sensitive component according to claim 16, wherein the radiation source is a luminescent diode and the detector means is a photodiode or phototransistor.

18. The chemically sensitive component according to claim 1, wherein the optical filter is a mixture of a triphenyl methane dye and a complementary acid selected from the group consisting of salicylic acid and bisphenol A.

19. The chemically sensitive component according to claim 1 wherein the acidic basic color former is selected from the group consisting of crystal violet and bromothymol blue.

* * * * *